US009888889B2

(12) United States Patent
Hartkens et al.

(10) Patent No.: US 9,888,889 B2
(45) Date of Patent: Feb. 13, 2018

(54) INTERVENTIONAL IMAGING SYSTEM

(71) Applicants: Thomas Hartkens, Erlangen (DE); Thomas Redel, Poxdorf (DE)

(72) Inventors: Thomas Hartkens, Erlangen (DE); Thomas Redel, Poxdorf (DE)

(73) Assignee: Siemens Healthcare GmbH, Erlangen (DE)

(*) Notice: Subject to any disclaimer, the term of this patent is extended or adjusted under 35 U.S.C. 154(b) by 229 days.

(21) Appl. No.: 14/013,152

(22) Filed: Aug. 29, 2013

(65) Prior Publication Data

US 2015/0018670 A1    Jan. 15, 2015

(30) Foreign Application Priority Data

Jul. 12, 2013    (DE) ........................ 10 2013 213 727

(51) Int. Cl.
*A61B 34/30*    (2016.01)
*A61B 6/12*    (2006.01)
(Continued)

(52) U.S. Cl.
CPC ................ *A61B 6/12* (2013.01); *A61B 6/486* (2013.01); *A61B 6/5217* (2013.01); *A61B 6/488* (2013.01);
(Continued)

(58) Field of Classification Search
CPC ............ A61B 19/5244; A61B 19/5225; A61B 2019/5251; A61B 2019/5255;
(Continued)

(56) References Cited

U.S. PATENT DOCUMENTS

2002/0133172 A1* 9/2002 Lambrecht ......... A61B 17/1703
606/130
2008/0013809 A1* 1/2008 Zhu et al. ..................... 382/128
(Continued)

FOREIGN PATENT DOCUMENTS

CN           102316816 A      1/2012
DE       102007045075 A1      4/2009
WO      WO 2010092512 A1      8/2010

*Primary Examiner* — Elmer Chao
(74) *Attorney, Agent, or Firm* — Lempia Summerfield Katz LLC

(57) ABSTRACT

An interventional medical diagnosis and/or therapy system is provided. The system provides an interventional imaging system and method which allows for an intervention, to be conducted in accordance with an intervention plan, to be supported and monitored by ongoing imaging, in particular radioscopy, with which, at the same time the effort in calibration and registration is kept low, and which functions without an additional location system. The interventional imaging system includes an imaging device to record intervention data of a body, at least two position markings, capable of being recorded with the imaging device, for the marking of an intervention instrument, a display apparatus to reproduce recorded intervention data and position markings, a navigation facility connected to the display apparatus to load pre-intervention data of the body, in which an intervention location of the body is contained, and for the mutual registration of the pre-intervention data with the intervention data.

12 Claims, 3 Drawing Sheets

(51) Int. Cl.
  *A61B 6/00* (2006.01)
  *A61B 34/20* (2016.01)
  *A61B 90/00* (2016.01)
(52) U.S. Cl.
  CPC .............. *A61B 6/5247* (2013.01); *A61B 34/20* (2016.02); *A61B 34/30* (2016.02); *A61B 2090/376* (2016.02); *A61B 2090/3966* (2016.02)
(58) Field of Classification Search
  CPC ...... A61B 2019/507; A61B 2019/5265; A61B 6/12; A61B 6/486; A61B 6/5217; A61B 6/488; A61B 6/5247; A61B 34/30; A61B 2090/3966; A61B 2090/376
  See application file for complete search history.

(56) References Cited

U.S. PATENT DOCUMENTS

| | | | |
|---|---|---|---|
| 2009/0082784 A1* | 3/2009 | Meissner | A61B 19/2203 606/130 |
| 2011/0060214 A1 | 3/2011 | Makower | |
| 2013/0345718 A1* | 12/2013 | Crawford | A61B 17/025 606/130 |

* cited by examiner

INTERVENTIONAL IMAGING SYSTEM

CROSS REFERENCE TO RELATED APPLICATIONS

The present application claims priority to German application No. 102013213727.3 DE filed Jul. 12, 2013, the entire content of which is hereby incorporated herein by reference.

FIELD OF INVENTION

The invention relates to an interventional medical diagnosis and/or therapy system.

BACKGROUND OF INVENTION

Interventional procedures, such as are applied, for example, in radiology, are today already playing an important part in the diagnosis and therapy of many illnesses. By way of example, certain instruments are used, such as needles, to reach a specific point in the body or inside an organ from the outside through the skin (percutaneous). This relates for instance to punctures, biopsies, ablations, or brachytherapies, or fixations, such as screws, are put in place.

Based on further technical developments of the imaging systems, the techniques referred to as modalities, such as, for example, computed tomography, magnetic resonance tomography, or angiography, are capable of identifying inflammatory or tumorous changes at increasingly early stages. In order to impose as little burden on the patient as possible, minimal-invasive interventions are increasingly frequently being carried out at very early stages, when the changes have still only extended over a comparatively small space. In addition, increasingly finer instruments are being developed for punctures, catheterization, and scanning of the organ systems. In order for increasingly smaller target regions in the body to be accessible with increasingly finer instruments, increasingly more precise and accurate navigation methods are also required.

Due to the fact that the physician cannot directly see the instrument in the body of the patient, he is reliant on the support of imaging methods. Ideally, the physician will have available, prior to the intervention, a 3D data record of a modality (e.g. magnetic resonance tomograph, computed tomograph, angiography device) in which he can identify the target region and, based on the physiology, can plan the ideal way to reach it, and therefore the entry point for the instrument. In a simpler variant, the target region will be identified during the intervention, for example by means of a C-arm X-ray device, which can produce CT images, and further planning can be undertaken on the basis of the combined information from 2D and 3D data from the X-ray device. With this planning, the entry point on the body and the orientation of the interventions instrument, e.g. a needle, can be determined.

In general, a planning of the entry route of the instrument is carried out by the physician by means of a planning system, i.e. by virtual means with the aid of software suited thereto, and then transferred manually to the interventional instrument, which can be carried out with robot support.

The intervention plan can then be passed to a navigation system, which is registered with the 3D data record. The navigation system can control or support the alignment of the instrument by means of a variety of different manual or automatic methods. The advance of the instrument can be monitored in this situation radioscopically, i.e. in real time under X-ray radioscopy or by ultrasound. As an alternative, the pre-interventional 3D data record can be co-registered with the C-arm data record, and the information then used for the navigation.

Problems arise, for example, in situations involving adipose or heavily-built patients. Due to the technical realization of the C-arm X-ray device, only a limited volume of the body can be reconstructed. It may therefore occur, for example, that the surface of the body is not included in the 3D data record. With virtual planning, in this situation the physician cannot identify where the insertion point is located, and whether the planned access path may possibly be unsuitable for the intervention due to the superimposition of bones or ribs.

At the present time, for example, a fine-needle biopsy or a thermoablation of a focal point in the liver by a percutaneous route is carried out in most cases under CT-monitoring. In this situation, the physician carrying out the procedure makes use for his access planning of a combination of the CT sectional image, of markers applied to the surface of the skin of the patient, and of the orientation assistance provided by a laser reticule located on the CT gantry.

With this procedure, the actual puncture and the advance of the instrument are carried out essentially manually by the physician. Depending on his degree of experience, a multiple puncture will be necessary in this situation. This procedure, as well as involving unpleasant effects for the patient, also incurs an increased risk of complications, such as bleeding, organ injury, or hematoma. In addition to this, the precision of the puncture is restricted with this procedure, in particular with very small target regions.

In order to achieve more precisely targeted instrument guidance, a number of other different navigation aids are used, such as, for example, optical or electromagnetic location systems, or the use of a stereotactical frame, the position of which in space is known, and which exhibits an apparatus for instrument guidance. This procedure, however, is elaborate. As well as this, the distal end of the instrument, away from the patient, can be monitored by location systems. This means, however, that account cannot be taken of deformations of the instrument, e.g. of the tip of a needle, caused due to resistances in the body, and which under certain circumstances may lead to a deviation from the puncture path.

From the publication DE 10 2007 045 075 A1 an interventional navigation system is known, which exhibits a multi-axle robot arm for guiding an instrument secured to it. The robot arm exhibits a yield movement control system, by means of which the robot arm can give way in a monitored manner in response to external force effects, such as manual forces. As a result, the instrument can be positioned by the user manually and at the same time be held automatically by the navigation system in the desired orientation and position or, respectively, on the desired path. To achieve this, 3D data from the patient, the robot arm, and the intra-operative imaging device must be mutually registered.

The prior art represented in DE 10 2007 045 075 A1 makes it possible, for example, for the physician conducting a biopsy to pre-position a robotic needle guide manually, and the robot then takes charge of the final placement and alignment of the needle. To achieve this, mention is made of an array of methods for position recognition, all of which are based on external location techniques (optical, electromagnetic navigation) or on a fixed mechanical registration. With mechanical registration, the intention is that the robot should be mounted in a fixed position relative to the C-arm system.

If such a system is to be used in the surgical environment, however, a number of limitations may arise. With procedures for the fixation of the vertebral column, for example, a plurality of screws are introduced into different vertebral bodies. With a fixed mechanical registering of the instrument holder, regular and elaborate calibration is necessary in order to guarantee exact positioning when introducing the screws. This calibration is prone to faults, since random mechanical effects on the instrument holder in the operating theater cannot be excluded. Because correct and exact calibration is necessary for the precise application of the screws, the calibration must accordingly be frequently repeated. This is time-consuming and not practicable in the operation environment.

If, instead of this, an additional external location technique (optical, electromagnetic navigation) is used, the patient must first be registered with the operation plan (e.g. planned screw position). The patient and the instrument holder must then be registered with the location technique. The large number of registration steps is elaborate and time-consuming. In addition to this, additional location systems must be omitted, since their hardware is often in the way, as well as prone to faults.

SUMMARY OF INVENTION

The object of the invention is to provide an interventional imaging system and method which allow for an intervention to be conducted in accordance with an intervention plan, to be supported and monitored by ongoing imaging, in particular radioscopy, with which at the same time the effort in calibration and registration can be kept low, and which functions without an additional location system.

The invention achieves this object by an imaging system and a method with the features of the independent claims.

A basic concept of the invention consists of an interventional imaging system comprising an imaging device for the acquisition of intervention data of a body, at least two position markings which can be recorded with the imaging device for the marking of an intervention instrument, a display apparatus for the reproduction of acquired intervention data and position markings, a navigation facility connected to the display apparatus for loading pre-intervention data of the body, in which an intervention location of the body is included, and for the mutual registration of the pre-intervention data with the intervention data, wherein the navigation facility is designed to reproduce the registered pre-intervention data, including the intervention location, jointly with the position markings, on the display apparatus, wherein the position markings are formed and can be arranged on a longitudinal intervention instrument in such a way that they mark positions, in particular coaxial positions, along the longitudinal axis of the intervention instrument, in such a way that, when the position markings on the display apparatus are aligned toward one another and toward the intervention location, the actual longitudinal axis of the intervention instrument is also aligned toward the actual intervention location. Due to the fact that only the position markers which can be easily acquired are continually recorded and reproduced on the display apparatus, doses can be spared during the recording, i.e. X-ray doses if the recording is being made with an X-ray imaging system. The relevant location information with regard to the target location is obtained in this situation from the registered pre-intervention data. In addition to the position markers, however, the intervention data can also be continually recorded and reproduced on the display apparatus.

An advantageous further development of the basic concept consists of the fact that the intervention data is 2D data.

Another advantageous further development of the basic concept consists of the fact that the pre-intervention data is 3D data.

Another advantageous further development of the basic concept consists of the fact that the pre-intervention data is also recorded during the intervention, but before the respective current part intervention, and is 3D data (e.g. 3D DynaCT).

Another advantageous further development of the basic concept consists of the fact that the imaging device is an X-ray device.

Another advantageous further development of the basic concept consists of the fact that the imaging system is a C-arm X-ray system, which can record 3D data, as a result of which, advantageously, an intrinsic registration is provided between the 2D and 3D data.

Another advantageous further development of the basic concept consists of the fact that the intervention instrument can be an instrument, instrument holder, or instrument guide.

A further basic concept of the invention consists of a method for interventional imaging comprising the steps:
recording of intervention data,
arrangement of at least two position markings on a longitudinal intervention instrument, wherein the position markings are formed and arranged on the intervention instrument in such a way that they mark positions, in particular coaxial positions, along the longitudinal axis of the intervention instrument, in such a way that, when the position markings are aligned toward one another on the display apparatus and toward the intervention location, the actual longitudinal axis of the intervention instrument is also aligned toward the actual intervention location,
recording of the position markings,
loading of pre-intervention data, in which an intervention location of the body is included,
mutual registration of the intervention data and pre-intervention data,
reproduction of the registered pre-intervention data, together with the intervention location, jointly with the position markings on a display apparatus.

Due to the fact that only the easily recordable position markers are continuously recorded and reproduced on the display apparatus, a dose can be spared during the recording, i.e. an X-ray dose in cases of recording with an X-ray imaging device. The relevant location information relating to the target location or intervention location respectively is obtained in this situation from the registered pre-intervention data. In addition to the position markers, however, the intervention data can also be continually recorded and reproduced on the display apparatus.

An advantageous further development consists of the intervention data being 2D data.

Another advantageous further development consists of the pre-intervention data being 3D data.

Another advantageous further development consists of the imaging device being an X-ray device.

Another advantageous further development of the basic concept consists of the fact that
on the basis of the position markings a current position and alignment of the intervention instrument will be automatically identified,
on the basis of the pre-intervention data and the intervention location, a deviation in the current position and alignment from a target position and target alignment of the intervention instrument will be automatically identified, and the deviation, or a movement proposal formed from this for the movement of the intervention instrument, will be represented on the display apparatus.

A basic concept of the invention in accordance with the foregoing explanations accordingly consists of the use of continuous interventional imaging (radioscopy) for the final and precise positioning of the instrument holding or guidance of an intervention instrument in accordance with a predetermined planning. As the imaging system, use is made preferentially of an X-ray system, e.g. a C-arm X-ray system. Accordingly, a system and method are described which allow for simple manual pre-positioning, which can be easily moved to and from the patient couch, function without previous calibration, registration, or a location system, and attain an extremely high degree of flexibility.

To achieve this, the instrument guidance system is provided with at least one, and better two, recordable markers, if appropriate also impervious to X-rays, as position markings, of which the shape and location in relation to one another are known. These markers can be designed as comparable to a backsight/foresight targeting facility. In an interventional image, they are identified by means from image processing and image recognition, and therefore their position and orientation relative to the interventional image are represented. If it is intended that the position and orientation of the markers or of the intervention instrument respectively should be calculated, then use may be made as calculation parameters, for example, of their size in the interventional image, their displacement in relation to one another, and/or their symmetry/offset. In the result of such a calculation, the current position and alignment of the intervention instrument can be compared with the position and alignment at the intervention location. The result of the comparison can in turn be displayed to the operator, or a movement proposal for the intervention instrument towards the intervention location can be determined and displayed, or such a movement proposal can be transferred to a control device for the automatic movement of the intervention instrument.

If a 2D image system is used, as is usual in radioscopy, then in the first instance the information about the height of the guide or the intervention instrument respectively is missing with regard to the imaging system or with regard to the intervention location respectively. The absence of this information is not of significance, however, if the image detector is aligned in such a way that the detector normals match with the planned intervention path. The height or the distance interval of the intervention instrument to the patient can then be monitored by the operator himself and, if appropriate, also manually controlled by him.

If required, however, the height of the guide can also be calculated from a further radioscopy image, if the orientation of the imaging system is changed. This may be necessary if the detector normals do not match with the planned intervention path (e.g. if the detector cannot move into this position, due, for example, to collision problems). The location, size, and shape of the markers can then be calculated in the detector image on the basis of the planning and the detector position registered in the planning, and can serve as the basis for the further positioning.

No registration at all is necessary, since, after an initial movement of the instrument holder, and therefore of the markers, from the position change in the interventional image, the relative movement of the instrument holder to the final planned alignment of the instrument holder can be calculated. Accordingly, the holder of the instrument, for example a robot, can be mounted on a cart for instance and simply moved to the patient couch as required.

An advantage accordingly lies in the fact that no close integration of a robot or intervention instrument holder with the imaging system, for example a C-arm-X-ray system, is necessary. Due to the fact that the image detector has been aligned along the planned intervention trajectory, the robot arm can determine the desired position of the intervention instrument holder exclusively on the basis of the interventional images, such as radioscopy images, for example. This means that the trajectory which has been planned in the image system does not need to be transferred itself onto the intervention instrument holding system, but can be determined by the interventional images alone.

The imaging itself can be carried out with an adjusted low image rate. Because the markers can be optimally recorded, i.e. impervious to X-rays in the case of an X-ray system, the fluoroscopic dose per image can also be substantially reduced.

The image transfer/transfer of the intervention planning from the imaging system or of the navigation facility respectively to the intervention instrument control system, for example a robot control system, can also be carried out wirelessly. In general, this concept can also be transferred onto a completely manual positioning arrangement. In this situation, preferentially, a mechanical manually-controllable holding device can be used.

BRIEF DESCRIPTION OF THE DRAWINGS

Further advantageous embodiments are derived from the dependent claims, as well as from the following description of exemplary embodiments on the basis of figures. The figures show:

DETAILED DESCRIPTION OF INVENTION

Figure 1:
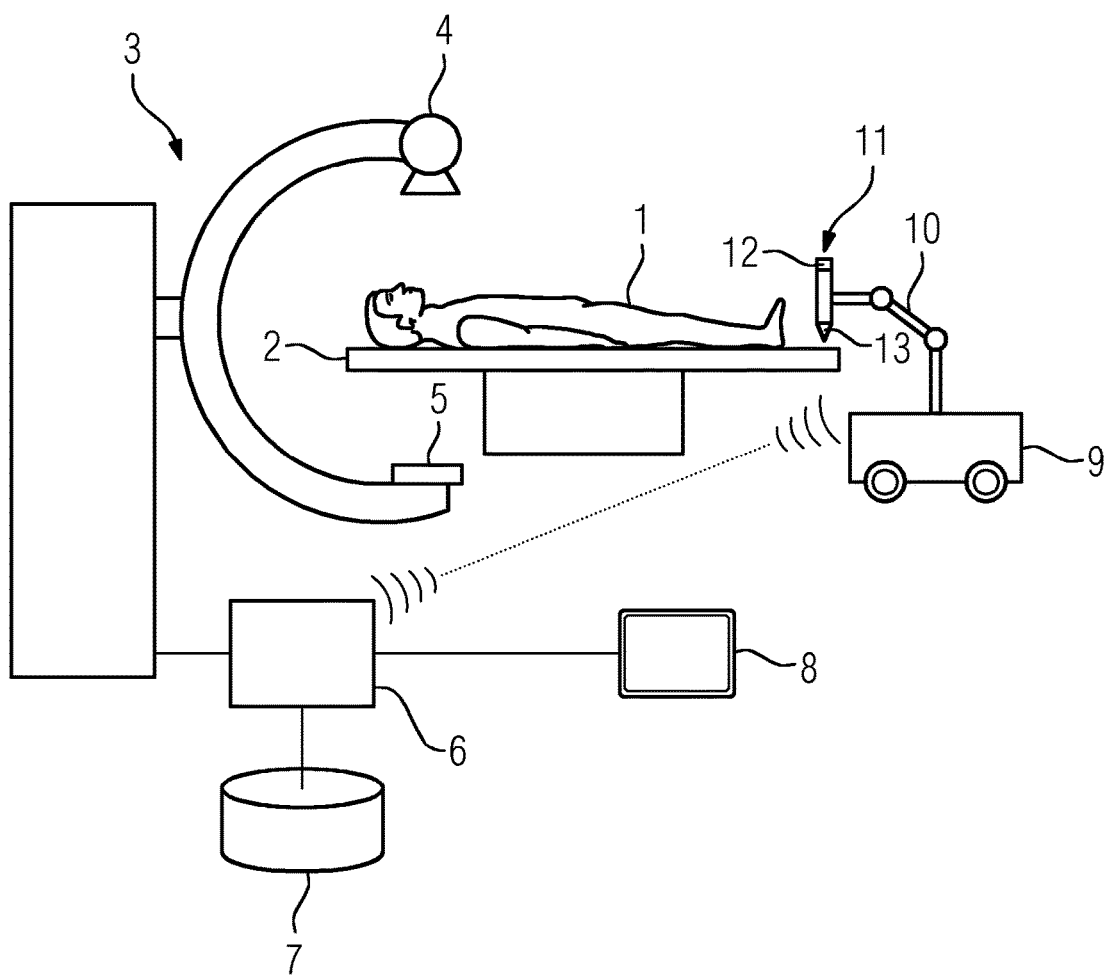
FIG. 1 Interventional imaging system,
FIG. 2 Position markings non-aligned,
FIG. 3 Position markings aligned,
FIG. 4 Position markings with movement proposal and
FIG. 5 Position markings before and after initial movement

Shown in diagrammatic form in FIG. 1 is an interventional imaging system. This comprises a C-arm X-ray system 3, a patient couch 2, and a cart 9 equipped for intervention purposes.

The C-arm X-ray system 3 comprises an X-ray emitter 4 and an image detector 5 arranged on a C-arm. It is connected to a navigation facility 6, which serves to support interventions which take place with the aid of interventional image data acquired by the C-arm X-ray system 3. According to a simple embodiment, intervention data is acquired in 2D by the C-arm X-ray system 3. In a more elaborate embodiment, however, 3D data can also be acquired, for which purpose the detector normals, which are derived from the position of the C-arm, must be rotated.

In order to carry out an intervention, the navigation facility 6 loads pre-intervention data from a corresponding data memory 7. The pre-intervention data is, as a rule, 3D data, which is acquired from a body which is to be treated before an intervention for planning the same. The pre-intervention data can be acquired with the most widely differing imaging methods, for example with CT, MRT, PET. It can also be acquired by the C-arm X-ray system 3 itself, which is provided for the intervention. Likewise, merged data records of different modalities can be used. The pre-intervention data comprises a representation of at least a part area of the body which is to be treated, which contains the actual intervention location. On the basis of the pre-intervention data, interventions can be planned at the intervention location in respect of their exact position as well as in respect of the access.

The navigation facility 6 registers the pre-intervention data loaded from the data memory 7 with the interventional data obtained from the C-arm X-ray system 3, which, for example, can be low-dose radioscopy data. By means of the registration it is guaranteed that an intervention location contained in the pre-intervention data can be exactly located in the interventional data. As well as this, by means of the registration the intervention location can be exactly located in the interventional data and therefore in the actual body of the patient, in order for an intervention to be carried out exactly at the intervention location in the body of the patient. The registered interventional and pre-interventional data is reproduced by the navigation facility 6 on a display device 8, for example a flat screen.

Located on a patient couch 2 is the body 1 of the patient who is to undergo an intervention. It is x-rayed by the C-arm X-ray system 3 in order to acquire interventional data. In particular, the C-arm or, respectively, the body 1 of the patient, is aligned in such a way that the intervention location of the body of the patient is contained in the interventional data. In consequence, previously acquired pre-intervention data is represented on the display device 8 together with intervention data acquired in real time.

In order for the intervention location in the body 1 of the patient, contained in the registered image data which is represented on the display device 8, to be approached and contacted as precisely as possible with an intervention instrument 11, the intervention instrument 11 is guided by a robot arm 10. The robot arm 10 can comprise a yield movement control system, such that the intervention instrument 11 can be guided manually by the operator. It may also be operated by remote control, such that an operator, by remote control of the robot arm 10, can control the intervention instrument 11 exactly. An automated embodiment is also conceivable, in which the robot arm 10 is controlled automatically by the navigation facility 6 on the basis of the pre-interventional and interventional image data.

In order to transfer planning and image data, or, respectively, to transfer further commands, a data link can be used between the cart 9 and the navigation facility 6. As an alternative, data can also be transferred onto the cart 9 before the intervention. A data link between the cart 9 and the navigation facility 6 can be provided in wireless form, as indicated in FIG. 1 by a broken line.

In order to be clearly visible in the interventional data, the intervention instrument 11 exhibits position markings 12, 13. These are formed in such a way that they can be easily recorded by the interventional imaging device. If the interventional imaging device is provided as an X-ray system, the position markings 12, 13 are therefore provided as impervious to X-rays. The position markings 12, 13 are explained in greater detail hereinafter.

Figure 2:
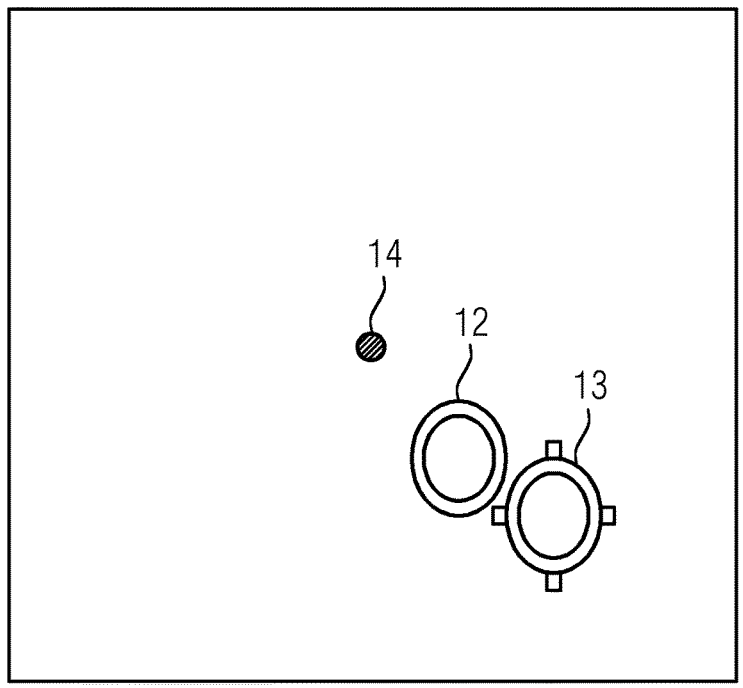

Represented in diagrammatic form in FIG. 2 is a reproduction of interventional and pre-interventional data, for example on the display device 8. On the basis of the pre-intervention data, the intervention location 14 is identified and marked. The interventional data is registered with the pre-interventional data, such that the intervention location 14 will therefore also be reproduced in the interventional data at the correct position. The image detector is aligned centrally and directly onto the intervention location 14.

While the intervention instrument itself is not identifiable in the interventional data, the position markings 12, 13 are easily visible. The position markings 12, 13 are designed as circular and arranged along the length of the intervention instrument, coaxially to its longitudinal axis. The position marking 12 is located on the side of the intervention instrument facing towards the intervention location 14, and the position marking 13 on the opposite side facing away from it.

The longitudinal axis of the intervention instrument is accordingly clearly identifiable, not aligned exactly onto the intervention location 14. An imaginary line running through the respective mid-points of the position markings 12, 13 corresponds to the longitudinal axis of the intervention instrument, and clearly does not run through the intervention location 14. In addition to this, it can be seen from the oval deformation of the image projection of the actual circular position markings 12, 13 that the intervention instrument is not aligned perpendicular to the image detector, i.e. in the detector normal, but is instead tilted.

Figure 3:
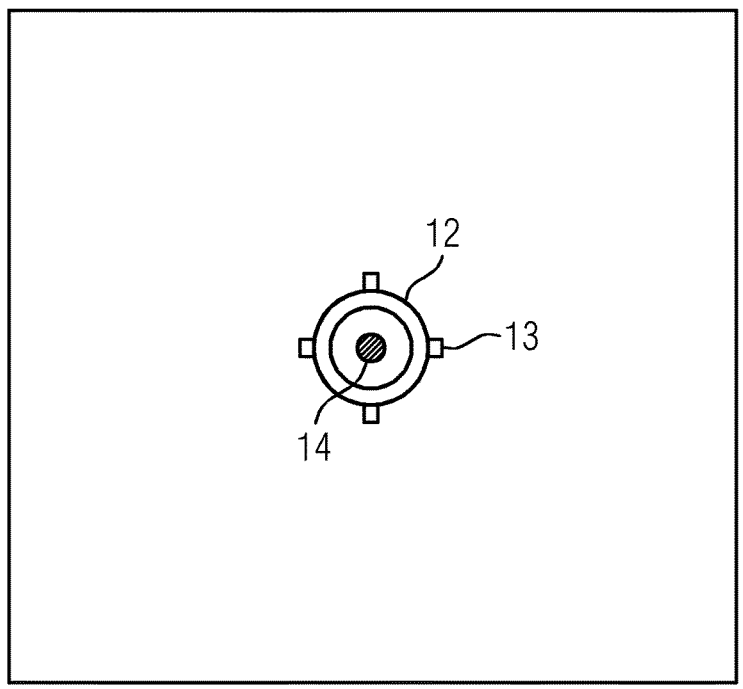

Represented diagrammatically in FIG. 3 is the pre-intervention data and intervention data explained heretofore, together with position markings 12, 13, with a changed positioning of the intervention instrument. The intervention location 14 is also located in the middle of the projection. As before, the image detector is aligned centrally onto the intervention location 14. The position markings 12, 13 are likewise located in the middle of the image. They are in alignment, such that the circular markings cover one another. Accordingly, the longitudinal axis of the intervention instrument is likewise arranged aligned exactly in the middle and onto the intervention location 14. Due to the fact that the intervention instrument is accordingly located in the middle of the image, and therefore also automatically perpendicular to the image detector, the projections of the circular position markings 12, 13 are therefore likewise circular.

From an oval deformation of the respective projection of the projection markings 12, 13 it can be clearly determined at what angle the intervention instrument is tilted in relation to the image detector normal. If the actual distance interval of the position markings 12, 13 from one another is known, a conclusion can also be drawn from the distance interval of the oval deformed projections of the position markings 12, 13, with the intervention instrument tilted in relation to the detector normals, with regard to the spatial position of the intervention instrument.

An increase in the precision of such a position determination can be achieved if an exactly known random movement of the intervention instrument is carried out, and two further positions and deformations of the position markings 12, 13 are then recorded. In this way, with the aid of the position markings 12, 13, with known geometry and arrangement of the intervention instrument, and, if appropriate, a known distance interval between the position markings 12, 13, as well as, if appropriate, known variation of location and alignment of the intervention instrument between two recordings, different exact position data of the intervention instrument can be determined.

Figure 4:
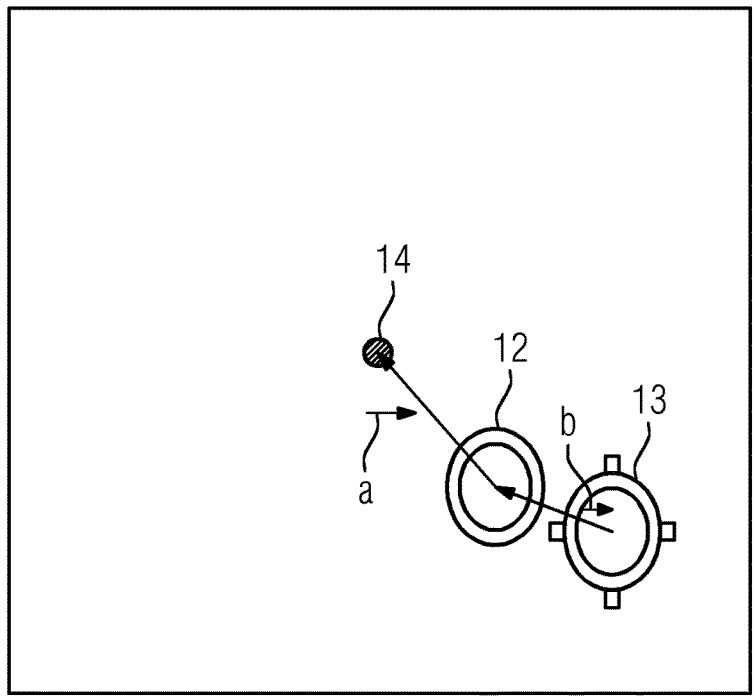

Represented in FIG. 4 are again interventional and pre-interventional data, together with the intervention location 14 and a respective projection of the position markings 12, 13. As before, the intervention location 14 is arranged in the middle, and the image detector aligned exactly onto it. The position markings 12, 13 are, as before, not arranged in the middle, and their projection is oval deformed. The intervention instrument is accordingly tilted in relation to the detector normal, and additionally not aligned onto the intervention location 14. Arrows a and b represent displacement vectors, which are intended to provide a more precise alignment of the intervention instrument onto the intervention location 14. By manual or automatic control of the intervention instrument in accordance with the displacement vectors a, b, the intervention location 14 could therefore be gradually approached with the intervention instrument.

Figure 5:
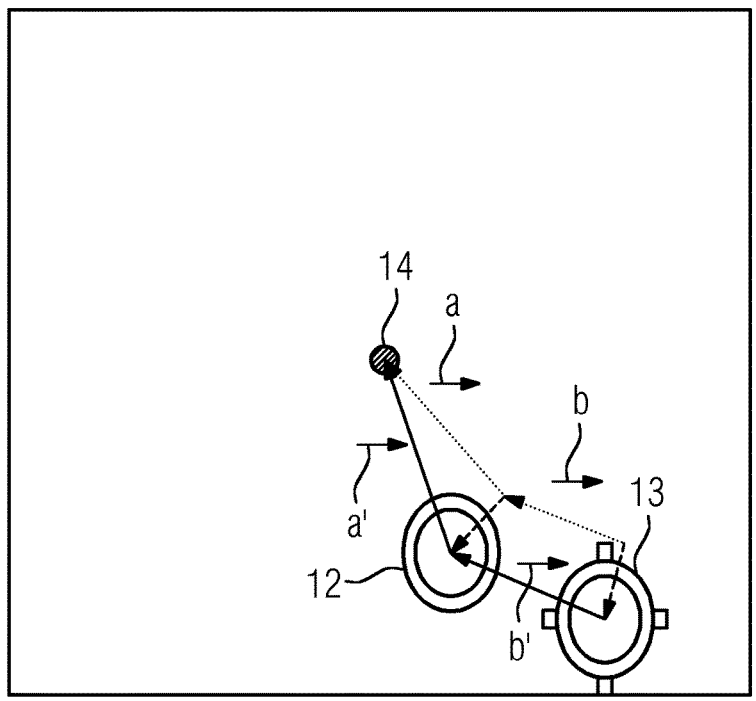

The intervention location 14 and the position markings 12, 13, are shown in FIG. 5 as heretofore. The position markings 12, 13 are arranged in a different position in comparison with the previous recording. This is incurred due to a previously-known random position change of the intervention instrument carried out in comparison with the previous position. With a previously-known random position change, and a known distance interval between the position markings 12, 13 at the intervention instrument, it is possible to acquire relatively precise position data for the intervention instrument from the position data of the position markings 12, 13 before and after the random movement. This includes in particular the z-axis, not contained in the 2D data, i.e. the distance interval of the intervention instrument from the intervention location 14 or from the image detector.

With the aid of the acquired data for the intervention instrument and of the momentary position which can be seen from the interventional and pre-interventional data, a movement proposal can be derived for the intervention instrument, by means of which this can be aligned more exactly onto the intervention location 14. Particularly by taking account of possible information relating to the position of the intervention instrument on the z-axis, i.e. the distance interval from the intervention location 14, however, it is possible in this situation for the required distance interval to the intervention location 14 or the body of the patient respectively to be maintained.

The exemplary embodiments described allow for the positioning, for example, of a screw, with pre-interventional planning available, taking the example of a drill sleeve with the following exemplary operating sequence A:
1. Manual positioning of the robot with the drill sleeve close to the patient couch
2. Manual rough positioning of the drill sleeve
3. Positioning of the C-arm X-ray system in such a way that the detector normal points towards the intervention location, or alternative calculation of the target position, size and shape of the markers on the radioscopy image
4. Start of the automatic positioning by the robot
5. Registration with the planning
   a. radioscopy recording and image recognition of the markers in the interventional radioscopy image
   b. Calculation of the relative position (x,y,z*) and initial movement proposal (delta_x,delta_y)
   c. Movement of the drill sleeve
   d. Radioscopy recording and image recognition of the markers in the interventional radioscopy image
   e. Calculation of the relative position change (dx,dy,dz), initial registration
6. Positioning/alignment of the sleeve
   a. Calculation of a new movement proposal (dx,dy)
   b. Movement of the drill sleeve
   c. Radioscopy recording and image recognition of the markers in the radioscopy image
   d. Repetition of steps 6a. to 6d. until final position/alignment is reached
7. Optional: Positioning of the sleeve at the planned distance interval from the object With regard to point 7): The positioning of the drill sleeve in the z direction towards the object is critical, because injury to the patient caused by the sleeve must be avoided. Accordingly (e.g. from the enlargement of the markers in point 5b), an initial distance interval from the detector and, if an intervention planning and 2D/3D registration is available, an initial distance interval from the patient is determined. This interval measurement is constantly improved in the course of the positioning with a large amount of data.

An alternative solution consists of automatically carrying out only the x,y positioning and alignment. If this is done, the physician brings the sleeve close to the object, using the yield movement controlled robot arm, wherein the robot only allows for a movement along the length of the detector normal.

A combination of both approaches is also conceivable. The physician guides the robot or the intervention instrument manually until he receives a signal to stop.

There are a number of different variants conceivable for the realization of the system as a whole:
1. The robot arm is fully integrated with the C-arm system, and is also actuated by this by way of an appropriate unit.
2. The robot arm has its own control unit (image recognition, image processing, and movement planning and controlling), and obtains from the C-arm system the pre-interventional planning data and interventional radioscopy images.
3. The control system of the robot arm contains the complete intervention planning, recognition, and control.
4. Both systems are fully separated. The planning takes place at the C-arm system. The C-arm is aligned in accordance with the planning (detector normal corresponds to the planned path). The control of the robot arm receives only the interventional radioscopy data. With the awareness of the alignment of the C-arm, navigation can be carried out without 3D data or planning data having to be transferred. Overall, the operational sequence appears as follows:
1. Preparation of a pre-interventional 3D data record of a patient with a medical imaging device (actuated by the physician)
2. Determination of a target region/intervention location of the patient which is to receive therapy, on the basis of the 3D data record (manually by the physician)
3. Planning of the intervention, e.g. drill holes in a vertebral column of the patient (also manually by the physician, possibly supported by a therapy planning system)
4. Transfer of the planning to the robot with the intervention instrument
5. Positioning of the intervention instrument, e.g. of a drill sleeve, in accordance with the workflow shown above, A)
6. Manual advance of the intervention instrument/drill by the operator; optional monitoring during the advance of the instrument (e.g. by means of radioscopy or interventional images produced by another imaging method)

We claim:
1. An interventional imaging system, comprising:
   an intervention instrument comprising at least two position markings;
   an imaging device that repeatedly records intervention data of a body including image projections of the position markings;
   a navigation facility that loads pre-intervention data of the body including image projection of an intervention location and mutually registers the pre-intervention data with the intervention data;

a display apparatus that displays the registered intervention data including the image projection of the intervention location and the image projections of the position markings of the intervention instrument; and a robot arm that is controlled by the navigation facility for guiding the intervention instrument until the image projections of the position markings cover one another and also cover the image projection of the intervention location displayed on the display apparatus, wherein the navigation facility repeatedly calculates position and orientation of the intervention instrument from the repeatedly recorded intervention data based on parameters comprising distance interval between the image projections of the position markings and/or geometry deformation of the image projections of the position markings in comparison with actually known distance interval between the position markings and known geometry of the position markings arranged on the intervention instrument, wherein the navigation facility repeatedly compares the calculated position and orientation of the intervention instrument with position and orientation of the intervention location, wherein the navigation facility repeatedly determines a movement proposal for the intervention instrument towards to the intervention location based on the comparison, and wherein the robot arm repeatedly guides a movement of the intervention instrument based on the repeatedly determined movement proposal until a final planned position and orientation of the intervention instrument aligns with the position and orientation of the intervention location.

2. The imaging system as claimed in claim 1, wherein the navigation facility is arranged such that, in addition to the pre-intervention data with the intervention location and the position markings, it also reproduces the intervention data on the display apparatus.

3. The imaging system as claimed in claim 1, wherein the intervention data is 2D data.

4. The imaging system as claimed in claim 1, wherein the pre-intervention data is 3D data.

5. The imaging system as claimed in claim 1, wherein the imaging device is an X-ray device.

6. The imaging system as claimed in claim 1, wherein the intervention instrument is an instrument holder, or an instrument guide.

7. A method for interventional imaging, comprising:

repeatedly recording intervention data of a body by an imaging device, wherein the intervention data comprises image projections of at least two position markings arranged on an intervention instrument;

loading pre-intervention data by a navigation facility, wherein the pre-intervention data comprises image projection of an intervention location of the body;

mutually registering the intervention data with the pre-intervention data by the navigation facility;

displaying the registered intervention data on a display apparatus; and controlling a robot arm by the navigation facility for guiding the intervention instrument until the image projections of the position markers cover one another and also cover the image projection of the intervention location displayed on the display apparatus, wherein the navigation facility repeatedly calculates position and orientation of the intervention instrument from the repeatedly recorded intervention data based on parameters comprising distance interval between the image projections of the position markings and/or geometry deformation of the image projections of the position markings in comparison with actually known distance interval between the position markings and known geometry of the position markings arranged on the intervention instrument, wherein the navigation facility repeatedly compares the calculated position and orientation of the intervention instrument with position and orientation of the intervention location, wherein the navigation facility repeatedly determines a movement proposal for the intervention instrument towards to the intervention location based on the comparison, and wherein the robot arm repeatedly guides a movement of the intervention instrument based on the repeatedly determined movement proposal until a final planned position and orientation of the intervention instrument aligns with the position and orientation of the intervention location.

8. The method as claimed in claim 7, wherein, in addition to the position markings, the intervention data is recorded and, together with the position markings and the pre-intervention data, reproduced on the display apparatus.

9. The method as claimed in claim 7, wherein the intervention data is 2D data.

10. The method as claimed in claim 7, wherein the pre-intervention data is 3D data.

11. The method as claimed in claim 7, wherein the imaging device is an X-ray device.

12. The method as claimed in claim 7, wherein on the basis of the position markings a current position and alignment of the intervention instrument is automatically identified, on the basis of the pre-intervention data and the intervention location, a deviation in the current position and orientation from a target position and alignment of the intervention instrument is automatically identified, and the deviation or the movement proposal formed from this for the movement of the intervention instruments is represented on the display apparatus.

\* \* \* \* \*